(12) United States Patent
Burman et al.

(10) Patent No.: US 7,094,755 B2
(45) Date of Patent: Aug. 22, 2006

(54) VASOACTIVE INTESTINAL PEPTIDE ANALOGS

(75) Inventors: Anand C. Burman, Ghaziabad (IN); Sudhanand Prasad, Ghaziabad (IN); Rama Mukherjee, Ghaziabad (IN); Anu T. Singh, Ghaziabad (IN); Archna Mathur, Ghaziabad (IN); Neena Gupta, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 141 days.

(21) Appl. No.: 10/254,569

(22) Filed: Sep. 25, 2002

(65) Prior Publication Data

US 2003/0158110 A1     Aug. 21, 2003

Related U.S. Application Data

(62) Division of application No. 09/630,335, filed on Jul. 31, 2000, now Pat. No. 6,489,297.

(30) Foreign Application Priority Data

Feb. 18, 2000   (IN)  .......................... 136/DEL/2000

(51) Int. Cl.
    *A61K 38/16*   (2006.01)
(52) U.S. Cl. .......................... 514/12; 530/324; 930/170
(58) Field of Classification Search .................. 514/12; 530/324

See application file for complete search history.

(56) References Cited

U.S. PATENT DOCUMENTS

| | | | |
|---|---|---|---|
| 4,605,641 A | 8/1986 | Bolin et al. | 514/12 |
| 4,734,400 A | 3/1988 | Bolin et al. | 514/12 |
| 4,835,252 A | 5/1989 | Musso et al. | 530/324 |
| 4,866,039 A | 9/1989 | Wootton et al. | 514/16 |
| 5,141,924 A | 8/1992 | Bolin | 514/12 |
| 5,217,953 A | 6/1993 | Gozes et al. | 514/12 |
| 5,376,637 A | 12/1994 | Sawai et al. | 514/12 |
| 5,428,015 A | 6/1995 | Kurono et al. | 514/12 |
| 5,565,424 A | 10/1996 | Gozes et al. | 514/12 |
| 5,677,419 A | 10/1997 | Bolin et al. | 530/317 |
| 5,849,261 A | 12/1998 | Dean et al. | 424/1.69 |
| 6,007,792 A | 12/1999 | Dean et al. | 424/1.69 |

FOREIGN PATENT DOCUMENTS

| | | |
|---|---|---|
| EP | 0796867 | 9/1997 |
| EP | 796867 | 9/1997 |
| EP | 0835662 | 4/1998 |
| WO | 9830590 | 7/1998 |
| WO | 0005260 | 2/2000 |

OTHER PUBLICATIONS

Jain, Rakesh, Delivery of Molecular Medicine to Solid Tumors, Science, vol. 271, pp. 1079-1080, Feb. 1996.*
Dermer, Gerald. Another Anniversary for the War on Cancer, Bio/technology, vol. 12, p. 320 Mar. 1994.*
Gura, Trisha. Systems for Identifying New Drugs Are Often Faulty, Science, vol. 278, pp. 1041-1042, Nov. 1997.*
Golden, Fredrick. OF Mice and Men: Don't Blame the Rodents, Time, pp. 44, May 1998.*
H. Frucht et al.; Characterization of Functional Receptors for Gastrointestinal Hormones on Human Colon Cancer Cells; Cancer Research 52; 1114-1122; Mar. 1, 1992.
Irene Virgolini et al.; Vasoactive Intestinal Peptide-Receptor Imagine for the Localization of Intestinal . . . Tumors; New England Journal of Medicine; vol. 331 (17); 1116-1121; Oct. 27, 1994.
G.Lilling et al.; Inhibition of Human Neuroblastoma Growth by a Specific VIP Antagonist; Journal of Molecular Neuroscience; vol. 5, 1994/1995; 231-239.
Gozes et al.; Vasoactive Intestinal Peptide Potentiates Sexual Behavior; Inhibition by Novel Antagonist Endocrinology; vol. 125, No. 6; 2945-2949; (1989).
Nokihara, K. et al. "Receptor Recognition of PACAP and VIP Examined by Binding Studies . . . " Peptides, (1996) pp. 63-66.
Dickinson, T. et al. "VIP and PACAP: very important in pain?" TIPS, (1999) vol. 20, No. 8, pp. 324-329.
Scholz, Catherine C., et al; Correlation of Drug Response in Patients and in the Clonogenic Assay with Solid Human Tumour Xenografts; Eur. J. Cancer; vol. 26, No. 8 pp. 901-905, 1990.
Giovanella, Beppino, et al; Correlation Between Response to Chemotherapy of Human Tumors in Patients and in Nude Mice; Cancer 52, pp. 1146-1152, 1983.
Fiebig, H.H., et al.; Clonogenic assay with established human tumour xenografts: correlation of in vitro to in vivo activity as a basis for anticancer drug discocery; European Journal of Cancer 40, pp. 802-820, 2004.
Johnson, JI, et al.; Relationships between drug activity in NCI preclinical in vitro and in vivo models and early clinical trials; British Journal of Cancer; vol. 84; No. 10;pp. 1424-1431; 2001.

* cited by examiner

*Primary Examiner*—Anish Gupta
(74) *Attorney, Agent, or Firm*—Ladas and Parry LLP

(57) ABSTRACT

The present invention encompasses novel analogs of vasoactive intestinal peptide (VIP), containing substitutions at appropriately selected amino acids. The invention particularly relates to the design and synthesis of novel biologically active VIP analogs containing α, α-dialkylated amino acids in a site-specific manner. Specifically, the invention relates to the synthesis of VIP peptide derivatives, which bind selectively to VIP receptors on target cells. The invention encompasses methods for the generation of these peptides, compositions containing the peptides and the pharmacological applications of these peptides especially in the treatment and prevention of cancer.

14 Claims, No Drawings

VASOACTIVE INTESTINAL PEPTIDE ANALOGS

This application is a division of Ser. No. 09/630,335 filed Jul. 31, 2000, now U.S. Pat. No. 6,489,297.

FIELD OF THE INVENTION

The present invention encompasses novel analogs of vasoactive intestinal peptide (VIP), containing substitutions at appropriately selected amino acids. The invention particularly relates to the design and synthesis of novel biologically active VIP analogs containing α, α-dialkylated amino acids in a site-specific manner. Specifically, the invention relates to the synthesis of VIP peptide derivatives, which bind selectively to VIP receptors on target cells. The invention encompasses methods for the generation of these peptides, compositions containing the peptides and the pharmacological applications of these peptides especially in the treatment and prevention of cancer.

BACKGROUND OF THE INVENTION

Vasoactive intestinal peptide is known to play critical roles in modulating the intracellular and extracellular events involved in homeostasis, and are intimately involved in all major cognitive and non-cognitive homeostatic systems (Schofl et al., 1994). The multiple biological activities of peptides has led to extensive research focused on the exploitation of these peptide hormones as therapeutic drugs. Multiple replacements have been used to avoid the susceptibility of the amide bond to proteolytic cleavage. These include the use of nonstandard amino acids like D-amino acids, N-alkyl and N-hydroxy-amino acids, α-aza amino acids, thioamide linkage, design of peptide mimetics and prodrugs as well as amide bond modifications under the pseudopeptide linkage rubric (Dutta, 1993; Pasternak et al., 1999). Another approach has been the blockage of N-terminus or C-terminus of the peptide by acylation or amidation.

Vasoactive intestinal peptide is a 28-amino acid neuropeptide, which was first isolated from the porcine intestine (Said and Mutt, 1970). It bears extensive homology to secretin, peptide histidine isoleucine (PHI) and glucagon. The amino acid sequence for VIP is

```
                                            (SEQ ID NO: 1)
His-Ser-Asp-Ala-Val-Phe-Thr-Asp-Asn-Tyr-Thr-Arg-
Leu-Arg-Lys-Gln-Met-Ala-Val-Lys-Lys-Tyr-Leu-Asn-
Ser-Ile-Leu-Asn-NH₂.
```

VIP is known to exhibit a wide variety of biological activities in the autocrine, endocrine and paracrine functions in living organisms (Said, 1984). In the gastrointestinal tract, it has been known to stimulate pancreatic and biliary secretions, hepatic glycogenesis as well as the secretion of insulin and glucagon (Kerrins and Said, 1972; Domschke et al., 1977). In the nervous system it acts as a neurotransmitter and neuromodulator, regulating the release and secretion of several key hormones (Said, 1984). In recent years, attention has been focussed on the function of VIP in certain areas of the CNS as well its role in the progression and control of neoplastic disease (Reubi, 1995).

The importance of peptide growth factors and regulatory hormones in the etiology and pathogenesis in several carcinomas has long been recognized. Data from epidemiological and endocrinological studies suggest that neuropeptides like VIP which are responsible for the normal growth of tissues like the pancreas can also cause conditions for their neoplastic transformation (Sporn et al., 1980). Several lines of evidence indicate that VIP acts as a growth factor and plays a dominant autocrine and paracrine role in the sustained proliferation of cancer cells (Said, 1984). The stimulatory effect of VIP on tumor growth can be mediated directly by its receptors on cell membranes or indirectly by potentiation of the activities of other growth factors in tumor cells (Scholar et al., 1991). The synergistic effect of VIP and related pituitary adenylate cyclase activating polypeptide (PACAP) in glioblastomas is an illustration to the above fact (Moody et al., 1996).

The multiple physiological and pharmacological activities of VIP are mediated by high affinity G-protein coupled transmembrane receptors on target cells (Reubi et al., 1996). VIP receptors are coupled to cellular effector systems via adenyl cyclase activity (Xia et al., 1996). The VIP receptor, found to be highly over expressed in neoplastic cells, is thought to be one of the biomarkers in human cancers (Reubi et al., 1996). High affinity VIP receptors have been localized and characterized in neoplastic cells of most breast carcinomas, breast and prostate cancer metastases, ovarian, colonic and pancreatic adenocarcinomas, endometrial and squamous cell carcinomas, non small cell lung cancer, lymphomas, glioblastomas, astrocytomas, meningiomas and tumors of mesenchymal origin. Amongst, neuroendocrine tumors all differentiated and non-differentiated gastroenteropancreatic tumors, pheochromocytomas, small-cell lung cancers, neuroblastomas, pituitary adenomas as well tumors associated with hypersecretory states like Verner-Morrison syndrome were found to overexpress receptors for vasoactive intestinal peptide (Tang et al., 1997a & b; Moody et al., 1998a & b; Oka et al., 1998)). These findings suggest that new approaches for the diagnosis and treatment of these cancers may be based on functional manipulation of VIP activity, by designing suitable peptide derivatives of the same.

The present invention relates to the anti-neoplastic activity of novel VIP peptide analogs using selected constrained amino acids. These novel VIP analogs were found to bind to VIP receptor on cell membranes. The anti-neoplastic activity of the aforesaid peptides was also determined.

The design of conformationally constrained bioactive peptide derivatives has been one of the widely used approaches for the development of peptide-based therapeutic agents. Non-standard amino acids with strong conformational preferences may be used to direct the course of polypeptide chain folding, by imposing local stereochemical constraints, in de novo approaches to peptide design. The conformational characteristics of α, α-dialkylated amino acids have been well studied. The incorporation of these amino acids restricts the rotation of φ, Ψ, angles, within the molecule, thereby stabilizing a desired peptide conformation. The prototypic member of α, α-dialkylated aminoacids, α-amino-isobutyric acid (Aib) or α, α-dimethylglycine has been shown to induce (β-turn or helical conformation when incorporated in a peptide sequence (Prasad and Balaram, 1984, Karle and Balaram, 1990). The conformational properties of the higher homologs of α, α-dialkylated amino acids such as di-ethylglycine (Deg), di-n-propylglycine (Dpg), di-n-butylglycine (Dbg) as well as the cyclic side chain analogs of α, α-dialkylated amino acids such as 1-aminocyclopentane carboxylic acid (Ac5c), 1-aminocyclohexane carboxylic acid (Ac6c), 1-aminocycloheptane carboxylic acid (Ac7c) and 1-aminocyclooctane carboxylic acid (Ac8c) have also been shown to induce folded conformation (Prasad et al., 1995; Karle et al., 1995). α, α-dialkylated amino acids have been used in the design of highly potent chemotactic peptide analogs (Prasad et al., 1996). The applicants are not aware of any prior art for the synthesis of novel peptide analogs, encompassed in the present invention. The present invention exploits the conformational properties of α, α-dialkylated amino acids for the design of biologically active peptide derivatives, taking VIP as the model system under consideration.

REFERENCES

Domschke, S. et al. (1977) Gastroenterology, 73, 478–480.
Dutta, A. S. (1993) Small Peptides: Chemistry, Biology and Clinical Studies, Elsevier,
Pharmacochemistry Library, 19, pp 293–350.
Karle, I. L. et al. (1995) J. Amer. Chem. Soc. 117, 9632–9637.
Karle, I. L. and Balaram, P. (1990) Biochemistry 29, 6747–6756.
Kerrins, C. and Said, S. I. (1972) Proc. Soc. Exp. Biol. Med. 142, 1014–1017.
Oka, H. et al. (1998) Am. J. Pathol. 153, 1787–1796.
Pasternak, A. et al. (1999) Biorg. Med. Chem. 9, 491–496.
Prasad, B V V and Balaram, P. (1984) CRC Crit. Rev. Biochem. 16, 307–347.
Prasad, S et al. (1995) Biopolymers 35, I 1–20
Prasad, S et al. (1996) Int. J. Peptide Protein Res. 48, 312–318.
Reubi, J. C. et al. Cancer Res., 56 (8), 1922–1931, 1996.
Said, S. I. and Mutt, V. (1970) Science, 169, 1217–1218.
Said, S. I. (1984) Peptides, 5, 143–150.
Scholar E. M. Cancer 67(6): 1561–1569, 1991.
Scofl, C. et al. (1994) Trends. Endocrinol. Metab. 5, 53–59.
Sporn, M. B., and Todaro, G. J. (1980) N. Engl. J. Med., 303, 378–379.
Stewart, J. and Young, Y. D. (1969) Solid Phase Peptide Synthesis, W. H. Freeman & Co.
Tang, C. et al., (1997a) Gut, 40, 267–271.
Tang, C. et al., (1997b) Br. J. Cancer, 75, 1467–1473.
Xia, M. et al., J. Clin. Immunol., 16 (1), 21–30, 1996

Throughout the specification and claims the following abbreviations are used with the following meanings:

| | |
|---|---|
| BOP: | Benzotriazole-1-yl-oxy-tris-(dimethylamino)-phosphonium hexfluorophosphate |
| PyBOP: | Benzotriazole-1-yl-oxy-tris-pyrrolidino-phosphonium hexofluorophospate |
| HBTU: | O-Benzotriazole-N,N,N',N'-tetramethyl-uronium-hexofluoro-phosphate |
| TBTU: | 2-(1H-Benzotriazole-1-yl)-1,1,3,3-tetra-methyluronium tetrafluoroborate |
| HOBt: | 1-Hydroxy Benzotriazole |
| DCC: | Dicyclohexyl carbodiimide |
| DIPCDI: | Diisopropyl carbodiimide |
| DIEA: | Diisopropyl ethylamine |
| DMF: | Dimethyl formamide |
| DCM: | Dichloromethane |
| NMP: | N-Methyl-2-pyrrolidinone |
| TFA: | trifluoroacetic acid |

Throughout the specification and claims the amino acid residues are designated by their standard abbreviations. Amino acids denote L-configuration unless otherwise indicated by D or DL appearing before the symbol and separated from it by a hyphen.

SUMMARY OF THE INVENTION

The present invention comprises VIP antagonists of the following general formula, wherein appropriate amino acids in VIP have been replaced by α, α-dialkylated amino acids in a specific manner. The invention also comprises the pharmaceutically acceptable salts of the antagonists of the following general formula:

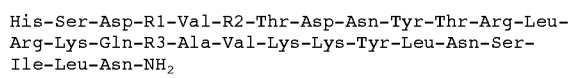

wherein
R1 is Aib, Deg or Ac5c,
R2 is Phe or 4-Cl-D-Phe,
R3 is Met, Leu or Dpg or a hydrolyzable carboxy protecting group;

or pharmaceutically acceptable salt of the antagonists.

DETAILED DESCRIPTION OF THE INVENTION

The present invention comprises VIP antagonists of the following general formula, wherein appropriate amino acids in VIP have been replaced by α, α-dialkylated amino acids in a specific manner. The invention also comprises the pharmaceutically acceptable salts of the antagonists of the following general formula:

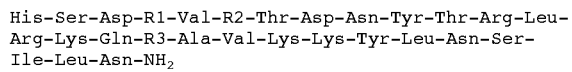

wherein
R1 is Aib, Deg or Ac5c,
R2 is Phe or 4-Cl-D-Phe,
R3 is Met, Leu or Dpg or a hydrolyzable carboxy protecting group;

or pharmaceutically acceptable salt of the antagonists.

A hydrolyzable carboxy protecting group are those groups which on hydrolysis converts to carboxy group such as —CONH$_2$, —COOMe, etc.

Salts encompassed within the term "pharmaceutically acceptable salts" refer to non-toxic salts of the compounds of this invention. Representative salts and esters include the following:

acetate, ascorbate, benzenesulfonate, benzoate, bicarbonate, bisulfate, bitartrate, borate, camsylate, carbonate, citrate, dihydrochloride, methanesulfonate, ethanesulfonate, ρ-toluenesulfonate, cyclohexylsulfamate, quinate, edetate, edisylate, estolate, esylate, fumarate, gluconate, glutamate, glycerophophates, hydrobromide, hydrochloride, hydroxynaphthoate, lactate, lactobionate, laurate, malate, maleate, mandelate, mesylate, mucate, napsylate, nitrate, n-methylglucamine, oleate, oxalate, palmoates, pamoate (embonate), palmitate, pantothenate, perchlorates, phosphate/diphosphate, polygalacturonate, salicylates, stearate, succinates, sulfate, sulfamate, subacetate, succinate, tannate, tartrate, tosylate, trifluoroacetate, and valerate.

Other salts include Ca, Li, Mg, Na, and K salts; salts of amino acids such as lysine or arginine; guanidine, diethanolamine or choline; ammonium, substituted ammonium salts or aluminum salts.

The salts are prepared by conventional methods.

The preferred VIP antagonists of the present invention are as follows:

(R1=Aib, R2=4-D-Cl-Phe, and R3=Leu):
His-Ser-Asp-Aib-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu -Asn-NH$_2$ (SEQ ID NO: 2);

(R1=Deg, R2=4-Cl-D-Phe, and R3=Leu):
His-Ser-Asp-Deg-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO: 3);

(R1=Ac5c, R2=4-Cl-D-Phe, and R3=Leu):
His-Ser-Asp-Ac5c-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO: 4);

(R1=Aib, R2=Phe, and R3=Met):
His-Ser-Asp-Aib-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH$_2$ (SEQ ID NO: 5);

(R1=Aib, R2=Phe, and R3=Leu):
His-Ser-Asp-Aib-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$, (SEQ ID NO: 6);

(R1=Ac5c, R2=Phe, and R3=Leu):
His-Ser-Asp-Ac5c-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO: 7);

(R1=Deg, R2=Phe, and R3=Leu):
His-Ser-Asp-Deg-Val-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO: 8);

(R1=Aib, R2=Phe, and R3=Dpg):
His-Ser-Asp-Aib-Val-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-NH$_2$ (SEQ ID NO: 9);

(R1=Aib, R2=4-Cl-D-Phe, and R3=Dpg):
His-Ser-Asp-Aib-Val-4-Cl-D-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-NH$_2$ (SEQ ID NO: 10);

(R1=Deg, R2=Phe, and R3=Dpg):
His-Ser-Asp-Deg-Val-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-NH$_2$ (SEQ ID NO: 11);

(R1=Ac5c, R2=Phe, and R3=Dpg):
His-Ser-Asp-Ac5c-Val-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-NH$_2$ (SEQ ID NO: 12).

The novel compounds of the present invention have important pharmacological applications. They are potent anti-neoplastic agents and thereby possess therapeutic potential in a number of human cancers.

Suitable routes of administration are those known in the art and include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

Pharmaceutical compositions suitable for use in present invention include compositions wherein the active ingredients are contained in an effective amount to achieve its intended purpose. The term "an effective amount" means that amount of a drug or pharmaceutical agent that will elicit the biological or medical response of a tissue, system, animal or human that is being sought.

In addition to the active ingredients, these pharmaceutical compositions may contain suitable pharmaceutically acceptable carriers excipients, diluents, solvents, flavorings, colorants etc. The preparations may be formulated in any form including but not limited to tablets, dragees, capsules, powders, syrups, suspensions, slurries, time released formulations, sustained release formulations, pills, granules, emulsions, patches, injections, solutions, liposomes and nanoparticles.

The exact formulation, route of administration and dosage can be chosen by the individual physician in view of the patient's condition.

Toxicity and therapeutic efficacy of the peptides of this invention can be determined by standard pharmaceutical procedures in cell cultures or experimental animals.

The novel peptide analogs embodied in the present invention contain amino acids, namely α, α-dialkylated amino acids, which have been known to induce highly specific constraints in the peptide backbone.

The α, α-dialkylated amino acids, used in the present invention are synthesized from the corresponding ketones. In a preferred embodiment of the invention, the ketones are first converted into the corresponding hydantoins, which are hydrolyzed using a strong acid or base, preferably $H_2SO_4$, HCl, NaOH, or $Na_2CO_3$ to yield the aforesaid amino acids. In a preferred embodiment of the present invention, 60% sulphuric acid has been employed as the hydrolyzing agent. The conversion of the ketones to their appropriate α, α-dialkylated amino acids is shown in Example 1.

The novel peptides in the present invention have been generated by using solid phase techniques or by a combination of solution phase procedures and solid phase techniques or by fragment condensation (Stewart and Young, 1969).

In a preferred embodiment of the present invention the peptides were synthesized using the Fmoc strategy, on a semi automatic peptide synthesizer (CS Bio, Model 536), using optimum side chain protection. The peptides were assembled from C-terminus to N-terminus. Peptides amidated at the carboxy-terminus were synthesized using the Rink Amide resin. The loading of the first Fmoc protected amino acid was achieved via an amide bond formation with the solid support, mediated by Diisopropylcarbodiimide (DIPCDI) and HOBt. Substitution levels for automated synthesis were preferably between 0.2 and 0.6 mmole amino acid per gram resin. The steps involved in the synthesis of the VIP analogs employed the following protocol:

TABLE I

| STEP | REAGENT | MIX TIME (MIN) | NO. OF CYCLES |
|---|---|---|---|
| 1. | Methylene chloride | 1 | 2 |
| 2. | Dimethyl formamide | 1 | 1 |
| 3. | 20% Piperidine in Dimethyl formamide | 1 | 1 |
| 4. | 20% Piperidine in Dimethyl formamide | 29 | 1 |
| 5. | Dimethyl formamide | 1 | 3 |
| 6. | Isopropanol | 1 | 2 |
| 7. | Methylene chloride | 1 | 2 |
| 8. | Amino Acid | Variable | 1 |
| 9. | Dimethyl formamide | 1 | 2 |
| 10. | Stop or Return for next cycle | | |

The resin employed for the synthesis of carboxy-terminal amidated peptide analogs was 4-(2',4'-Dimethoxyphenyl-Fmoc-aminomethyl)-phenoxymethyl derivatized polystyrene 1% divinylbenzene (Rink Amide) resin (100–200 mesh), procured from Calbioichem-Novabiochem Corp., La Jolla, U.S.A., (0.47 milliequivalent NH$_2$/g resin).

The present invention also provides a solid phase synthesis process for the preparation of a peptide analog of formula (I):

```
His-Ser-Asp-R1-Val-R2-Thr-Asp-Asn-Tyr-Thr-Arg-Leu-
Arg-Lys-Gln-R3-Ala-Val-Lys-Lys-Tyr-Leu-Asn-Ser-
Ile-Leu-Asn-NH2
``` wherein
R1 is Aib, Deg or Ac5c,
R2 is Phe or 4-Cl-D-Phe,
R3 is Met, Leu or Dpg,
which comprises sequentially loading the corresponding protected α-α-dialkylated amino acids in sequential cycles to the amino terminus of a solid phase resin, coupling the amino acids in the presence of conventional solvents and reagents to assemble a peptide-resin assembly, removing the protecting groups and cleaving the peptide from the resin to obtain a crude peptide analog.

In a particularly preferred embodiment of the present invention the following chemical moieties were used to protect reactive side chains of the peptides during the synthesis procedure.

The N-terminal amino group was protected by 9-fluorenylmethoxy-carbonyl group. Trityl (trt) or t-butyloxycarbonyl (Boc) were the preferred protecting groups for imadazole group of Histidine residue. The hydroxyl groups of Serine, Threonine and Tyrosine were preferably protected by t-butyl group (tBu) 2,2,5,7,8-pentamethyl-chroman-6-sulfonyl (Pmc) or 2,2,4,7,-pentamethyl-dihydrobenzenofuran-5-sulfonyl (Pbf) were the preferred protecting groups for the guandino group of Arginine. Trityl was the preferred protecting group for Asparagine and Glutamine and tertiary butyl group (tBu) was the preferred protecting group for Aspartic acid and Glutamic acid. The tryptophan residue was either left unprotected or used with Boc protection. The side chain amino group of Lysine was protected using preferably Boc group.

In a preferred embodiment of the invention, 2–8 equivalents of Fmoc protected amino acid per resin nitrogen equivalent were used. The activating reagents used for coupling amino acids to the resin, in solid phase peptide synthesis, are well known in the art. These include DCC, DIPCDI, DIEA, BOP, PyBOP, HBTU, TBTU, and HOBt. Preferably, DCC or DIPCDI/HOBt or HBTU/HOBT and DIEA were used as activating reagents in the coupling reactions.

The protected amino acids were either activated in situ or added in the form of preactivated esters known in the art such as NHS esters, Opfp esters etc Atherton, E. et al., 1988, J. Chem.Soc., Perkin Trans. I, 2887; Bodansky, M in "The Peptides, Analysis, Synthesis and Biology (E. Gross, J, Meienhofer, eds) Vol. 1, Academic Press, New York, 1979, 106.

The coupling reaction was carried out in DMF, DCM or NMP or a mixture of these solvents and was monitored by Kaiser test (Kaiser et al., Anal. Biochem., 34, 595–598 (1970)). In case of a positive Kaiser test, the appropriate amino acid was re-coupled using freshly prepared activated reagents.

After the assembly of the peptide analog was completed, the amino-terminal Fmoc group was removed using steps 1–6 of the above protocol and then the peptide resin was washed with methanol and dried. The analogs were then deprotected and cleaved from the resin support by treatment with a cleavage mixture of trifluoroacetic acid, crystalline phenol, ethanedithiol, thioanisole and de-ionized water for 1.5 to 5 hours at room temperature. The crude peptide was obtained by precipitation with cold dry ether, filtered, dissolved, and lyophilized.

The resulting crude peptide was purified by preperative high performance liquid chromatography (HPLC) using a LiChrOCART® $C_{18}$ (250. Times. 10) reverse phase column (Merck, Darmstadt, Germany) on a Preparative HPLC system (Shimadzu Corporation, Japan) using a gradient of 0.1% TFA in acetonitrile and water. The eluted fractions were reanalyzed on Analytical HPLC system (Shimadzu Corporation, Japan) using a $C_{18}$ LiChrospher®, WP-300 (300×4) reverse-phase column. Acetonitrile was evaporated and the fractions were lyophilized to obtain the pure peptide. The identity of each peptide was confirmed by electron-spray mass spectroscopy.

An analog of the present invention can be made by exclusively solid phase techniques, by partial solid phase/solution phase techniques and/or fragment condensation. Preferred, semi-automated, stepwise solid phase methods for synthesis of peptides of the invention are provided in the examples discussed in the subsequent section of this document.

The present invention will be further described in detail with reference to the following examples, as will be appreciated by a person skilled in the art is merely illustrative and should not be construed as limiting. Various other modifications of the invention will be possible without departing from the spirit and scope of the present invention.

Synthesis of Amino Acids

α, α-dialkylated amino acids were synthesized from the appropriate ketones. These ketones were first converted into their corresponding hydantoins which on hydrolysis with strong acid or alkali such as $H_2SO_4$, HCl, NaOH or $Na_2CO_3$ gave the respective amino acids.

EXAMPLE 1

Cyclopentanone (0.1 mol), KCN (0.3 mol) and $(NH_4)_2CO_3$ were dissolved in 300 ml of 50% aqueous methanol and the mixture was refluxed for 4–6 hrs on water bath. Subsequently, the solution was concentrated to half of its volume and chilled in an ice bath. The chilled solution was acidified with 2N HCl. The precipitate thus obtained was filtered and washed several times with cold water to remove the traces of cyanide. The solid was subsequently dried and recrystallized from aqueous alcoholic solution. The yield of the product in the aforesaid reaction was found to be 86%. The 5,5'-spirocyclopentane hydantoin thus obtained was characterized by I.R. spectroscopy (stretching bands characteristic of the carbonyl group were observed at 1710–1740 cm$^{-1}$ and 1760–1780 cm$^1$ respectively).

The 5,5'-spirocyclopentane hydantoin (0.05 mol) was dissolved in 45 ml of 60% $H_2SO_4$ and refluxed at 150–160° C. for about 28 hrs. The reaction mixture was cooled to room temperature and diluted with water (150 ml). The diluted solution was filtered to remove the charred particles. The clear solution was chilled in ice cold water and neutralized with ammonia solution. The solution was further concentrated and cooled. Shining white precipitate was obtained. The precipitate thus obtained was filtered and dried. The amino acid i.e. 1-aminocyclopentane carboxylic acid (Ac5c) was confirmed by I.R spectroscopy (1610–1640 cm$^{-1}$ for COO$^-$ group and 3060–3090 cm$^1$ for NH$_3^+$group).

EXAMPLE 2

Preparation of Fmoc-Asn(trt)-Resin

A typical preparation of the Fmoc-Asn(trt)-Resin was carried out using 0.5 g of 4-(2',4'-Dimethoxyphenyl-Fmoc-aminomethyl) phenoxymethyl-derivatized polystyrene 1% divinylbenzene (Rink Amide) resin (0.47 mM/g) (100–200 mesh), procured from Calbiochem-Novabiochem Corp., La Jolla, U.S.A. Swelling of the resin was typically carried out in dichloromethane measuring to volumes 10–40 mL/g resin. The resin was allowed to swell in methylene chloride (2×25 ml, for 10 min.). It was washed once in dimethylformamide (DMF) for 1 min. All solvents in the protocol were added in 20 ml portions per cycle. The Fmoc-protecting group on the resin was removed by following steps 3–7 in the protocol. The deprotection of the Fmoc group was checked by the presence of blue beads in the Kaiser test. For loading of the first amino acid on the free amino ($NH_2$) group of the resin, the first amino acid, Fmoc-Asn(trt)OH, was weighed in four fold excess, along with a similar fold excess of HOBt, in the amino acid vessel of the peptide synthesizer. These were dissolved in dimethylformamide (A.C.S. grade) (J. T. Baker, Phillipsburg, N.J., U.S.A.) and activated with DIPCDI, just prior to the addition to the resin in the reaction vessel of the peptide synthesizer. HOBt was added in all coupling reactions, especially in the case of Arg, Asn, Gln and His. The coupling reaction was carried out for a period ranging from 1–3 hours. The loading of the amino acid on the resin was confirmed by the presence of colorless beads in the Kaiser Test. The loading efficiency was ascertained by the increase of weight of the resin after the addition of the amino acid.

EXAMPLE 3

Synthesis of SEQ ID NO: 2 ($Aib^4$, 4-Cl-D-$Phe^6$, $Leu^{17}$,)-VIP His-Ser-Asp-Aib-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-$NH_2$ The synthesis of ($Aib^4$, 4-Cl-D-$Phe^6$,$Leu^{17}$,)-VIP, amidated at the carboxy terminus, was initiated by using all of the resin loaded with Fmoc-Asn(trt)-OH as prepared in Example 2 above. This was subjected to stepwise deprotection and coupling steps as in steps 1–10 of the synthesis cycle. In each coupling reaction, a four fold excess of amino-acid, DIPCDI and HOBt were used.

Upon completion of synthesis and removal of the N-terminal Fmoc protecting group (steps 1–6 of the synthesis cycle), the peptide-resin was washed twice with methanol, dried and weighed to obtain 0.649 g. This was subjected to cleavage in a cleavage mixture consisting of trifluoroacetic acid and scavengers, crystalline phenol, ethanedithol, thioanisole and water for a period of 3–5 hours at room temperature with continuous stirring. The peptide was precipitated using cold dry ether to obtain ~330 mg of crude peptide. The crude peptide was purified on a $C_{18}$ preparative reverse phase HPLC column (250×10) on a gradient system comprising acetonitrile and water in 0.1% TFA as described previously, in the art. The prominent peaks were collected and lyophilized, reanalyzed on analytical HPLC and subjected to mass spectrometry. There was a good agreement between the observed molecular weight and calculated molecular weight. The pure peptide was then used for bioassays.

EXAMPLE 4

Synthesis of SEQ ID NO: 5 [$Aib^4$]-VIP His-Ser-Asp-Aib-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-$NH_2$ A 0.255 g portion of Fmoc-Asn (trt)-Rink Amide resin from Example 2 was subjected to solid phase synthesis using the protocol stated in "Detailed Description of the Invention". All couplings were performed using the appropriate molar excess of the required Fmoc-amino acids. Coupling reagents and additives were used as well known to those skilled in the art. After the assembly of the peptide was complete the Fmoc group was removed from the resin, as mentioned earlier. The peptide was cleaved, lyophilized, purified and characterized according to the protocols described in the previous section.

EXAMPLE 5

Synthesis of Analogy SEQ ID NO: 9 [$Aib^4$, $Dpg^{17}$]-VIP His-Ser-Asp-Aib-Val-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-$NH_2$ A 0.255 g portion of Fmoc-Asn (trt)-Rink Amide resin from Example 2 was subjected to solid phase synthesis using the protocol stated in "Detailed Description of the Invention". All couplings were performed using the appropriate molar excess of the required Fmoc-amino acids. Coupling reagents and additives were used as well known to those skilled in the art. In a preferred embodiment of the invention, twenty seven coupling cycles were performed using appropriately protected amino acids as according to the sequence mentioned above. After the assembly of the peptide was complete the Fmoc group was removed from the resin, as mentioned earlier. The peptide was cleaved, lyophilized, purified and characterized according to the protocols described in the previous section.

EXAMPLE 6

The cytotoxic activity of synthesized peptides was tested on six human tumor cell lines namely PA-1 (ovary), SW620 (colon) HuTu8O (duodenum), L132 (lung), U87MG (glioblastoma), KB (oral), MIAPaCa2(pancreas), A549(non small cell lung) and HT-29(colon). The tumor cells were collected at exponential growth phase and resuspended in medium (1.5×10$^6$ cells/ml in RPMI 1640 containing 10% FBS). 150 µl of medium was added to the wells of a 96-well tissue culture plate (Nunc, Denmark) followed by 30 µl of cell suspension. The plate was left in incubator (37° C., 5% $CO_2$) overnight. 20 µl of the peptide (100 pM to 1 uM concentration) was added to marked wells of the 96-well plate. Each concentration was plated in triplicates. 20 µl of medium alone was added to control wells while wells without cells served as blanks. A total volume of 200 µl was ensured in each well and plate was left in incubator (37° C., 5% $CO_2$). After 72 hours of incubation an MTT assay was performed and percentage cytotoxicity was calculated with respect to control cells. Following Tables show the maximum cytotoxicity achieved on various cell lines.

| Cell Line | Percentage cytotoxicity at different concentrations | | | | |
|---|---|---|---|---|---|
| | 1 μM | 100 nM | 10 nM | 1 nM | 100 pM |

(SEQ ID NO: 2)
His-Ser-Asp-Aib-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$

| Cell Line | 1 μM | 100 nM | 10 nM | 1 nM | 100 pM |
|---|---|---|---|---|---|
| PA1 | 16.5 ± 3.4 | 18.9 ± 4.2 | 28.9 ± 5.5 | 30.0 ± 6.7 | 16 ± 3.3 |
| SW620 | 18.5 ± 5.1 | 23 ± 3.8 | 30 ± 4.5 | 28 ± 6.6 | 16.9 ± 4.5 |
| HuTu80 | 39 ± 4.5 | 24 ± 5.6 | 18 ± 4.5 | 20 ± 5.5 | 10 ± 3.5 |
| L132 | 15.9 ± 7.5 | 18.9 ± 5.0 | 30.9 ± 7.0 | 28 ± 4.5 | 18 ± 2.3 |
| U87MG | 14 ± 4.5 | 19.0 ± 7.0 | 28.9 ± 5.6 | 12 ± 7.6 | 10.5 ± 4.5 |
| KB | 43 ± 0.5 | 37 ± 5.0 | 34 ± 6.0 | 42 ± 8.0 | 47 ± 8.5 |
| MIAPaCa2 | 36 ± 0.5 | 32 ± 4.5 | 35 ± 3.5 | 31 ± 5.0 | 20 ± 6.5 |
| A549 | 45 ± 5.5 | 41 ± 6.0 | 21 ± 5.5 | 19 ± 4.5 | 16 ± 5.5 |
| HT29 | 38 ± 5.5 | 30 ± 5.8 | 25 ± 4.5 | 25 ± 4.5 | 26 ± 5.5 |

(SEQ ID NO: 3)
His-Ser-Asp-Deg-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$

| Cell Line | 1 μM | 100 nM | 10 nM | 1 nM | 100 pM |
|---|---|---|---|---|---|
| PA1 | 22.1 ± 4.5 | 23.5 ± 5.2 | 22 ± 4.5 | 29 ± 5.8 | 15 ± 4.5 |
| SW620 | 16 ± 3.4 | 22 ± 7.3 | 27 ± 5.5 | 29 ± 5.6 | 15.9 ± 6.6 |
| HuTu80 | 14.5 ± 7.1 | 24 ± 7.8 | 28 ± 4.7 | 29 ± 6.2 | 14 ± 7.8 |
| L132 | 14 ± 6.5 | 26 ± 6.5 | 29 ± 6.7 | 23 ± 3.5 | 14 ± 5.6 |
| U87MG | 25 ± 4.6 | 26 ± 6.7 | 28 ± 7.5 | 16 ± 6.6 | 11 ± 7.8 |
| KB | 14 ± 3.4 | 18 ± 8.5 | 22 ± 8.2 | 24.5 ± 9.5 | 13 ± 8.5 |

(SEQ ID NO: 4)
His-Ser-Asp-Ac5c-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$;

| Cell Line | 1 μM | 100 nM | 10 nM | 1 nM | 100 pM |
|---|---|---|---|---|---|
| PA1 | 21 ± 5.5 | 22.3 ± 4.5 | 23 ± 3.5 | 30 ± 6.0 | 16.1 ± 0.0 |
| SW620 | 15 ± 4.5 | 23 ± 6.7 | 28.5 ± 4.5 | 31 ± 6.5 | 16.9 ± 5.5 |
| HuTu80 | 15.5 ± 6.5 | 27 ± 7.9 | 27 ± 5.0 | 30 ± 7.0 | 11 ± 8.0 |
| L132 | 13 ± 4.5 | 28 ± 5.5 | 30 ± 5.5 | 27 ± 4.5 | 11 ± 8.0 |
| U87MG | 27 ± 5.5 | 28 ± 7.7 | 29 ± 6.7 | 15 ± 7.8 | 10 ± 4.6 |
| KB | 27 ± 4.3 | 26 ± 5.6 | 27 ± 7.8 | 30 ± 7.8 | 13 ± 8.0 |

(SEQ ID NO: 9)
His-Ser-Asp-Aib-Val-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-NH$_2$

| Cell Line | 1 μM | 100 nM | 10 nM | 1 nM | 100 pM |
|---|---|---|---|---|---|
| PA1 | 15.1 ± 2.3 | 17.4 ± 3.2 | 25.6 ± 4.5 | 27.8 ± 4.3 | 15.5 ± 3.3 |
| SW620 | 16.7 ± 4.1 | 21 ± 3.6 | 27 ± 3.4 | 28 ± 5.0 | 15.9 ± 4.5 |
| HuTu80 | 14.6 ± 5.1 | 23 ± 6.0 | 26 ± 5.5 | 28.5 ± 3.2 | 14.6 ± 2.7 |
| L132 | 13.6 ± 5.6 | 17.5 ± 5.5 | 18.9 ± 6.0 | 20 ± 0.0 | 17 ± 2.3 |
| U87MG | 12.5 ± 6.5 | 18.9 ± 6.5 | 26.7 ± 3.5 | 13.7 ± 3.6 | 11.5 ± 5.0 |
| KB | 10.5 ± 6.5 | 16.7 ± 5.1 | 16.7 ± 3.2 | 21.5 ± 4.5 | 13 ± 5.0 |

(SEQ ID NO: 10)
His-Ser-Asp-Aib-Val-4-Cl-D-Phe-Thr-Asp-Asn-Tyr-Thr-Arg-Leu-Arg-Lys-Gln-Dpg-Ala-Val-Lys-Lys-Tyr-Leu-Asn-Ser-Ile-Leu-Asn-NH$_2$

| Cell Line | 1 μM | 100 nM | 10 nM | 1 nM | 100 pM |
|---|---|---|---|---|---|
| PA1 | 23 ± 6.5 | 25 ± 5.0 | 26 ± 3.0 | 31 ± 6.0 | 28 ± 0.0 |
| SW620 | 16 ± 5.5 | 24 ± 7.3 | 29 ± 5.0 | 30 ± 6.5 | 17 ± 4.0 |
| HuTu80 | 16 ± 4.5 | 28 ± 8.0 | 28 ± 5.0 | 31 ± 7.0 | 15 ± 7.8 |
| L132 | 17 ± 5.0 | 29 ± 5.5 | 31 ± 6.0 | 28 ± 6.0 | 15 ± 7.0 |
| U87MG | 29 ± 4.0 | 29 ± 7.0 | 30.1 ± 4.0 | 16 ± 7.8 | 12 ± 5.0 |
| KB | 30 ± 5.0 | 27 ± 6.0 | 26 ± 7.8 | 32 ± 7.8 | 12 ± 8.0 |

All publications referenced are incorporated by reference herein, including the nucleic acid sequences and amino acid sequences listed in each publication. All the compounds and methods disclosed and referred to in the publications mentioned above are incorporated by reference herein, including those compounds disclosed and referred to in articles cited by the publications mentioned above.

What is claimed is:

1. A method for treating ovarian, colon, lung, oral, pancreatic, or non-small lung cancer, or cancer of the duodenum, or glioblastoma in a mammal comprising administering to the mammal an amount of a vasoactive intestinal peptide analog of the formula (I)

His-Ser-Asp-R1-Val-R2-Thr-Asp-Asn-Tyr-Thr-Arg-Leu-
Arg-Lys-Gln-R3-Ala-Val-Lys-Lys-Tyr-Leu-Asn-Ser-
Ile-Leu-Asn-NH₂ wherein

R1 is Aib, Deg or AcSc,

R2 is Phe or 4-Cl-D.-Phe,

R3 is Met, Leu or Dpg or a vasoactive intestinal peptide analog of the formula (I) having a hydrolyzable carboxyl protecting group; or a pharmaceutically acceptable salt thereof effective to treat the cancer.

2. The method according to claim 1 further comprising a chemotherapeutic compound.

3. The method according to claim 1 wherein R1 is Aib, R2 is 4-D-Cl-Phe, and R3 is Leu and said peptide is:

(SEQ ID NO:2)
His-Ser-Asp-Aib-Val-4-Cl-D-Phe-Thr-Asp-Asn-Tyr-
Thr-Arg-Leu-Arg-Lys-Gln-Leu-Ala-Val-Lys-Lys-Tyr-
Leu-Asn-Ser-Ile-Leu-Asn-NH₂ or a pharmaceutically acceptable salt thereof.

4. The method according to claim 1 wherein R1 is Deg, R2 is 4-Cl-D-Phe, and R3 is Leu and said peptide is:

(SEQ ID NO: 3)
His-Ser-Asp-Deg-Val-4-Cl-D-Phe-Thr-Asp-Asn-Tyr-
Thr-Arg-Leu-Arg-Lys-Gln-Leu-Ala-Val-Lys-Lys-Tyr-
Leu-Asn-Ser-Ile-Leu-Asn-NH₂ or a pharmaceutically acceptable salt thereof.

5. The method according to claim 1 wherein R1 is Ac5c, R2 is 4-Cl-D-Phe, and R3 is Leu and said peptide is:

(SEQ ID NO: 4)
His-Ser-Asp-Ac5c-Val-4-Cl-D-Phe-Thr-Asp-Asn-Tyr-
Thr-Arg-Leu-Arg-Lys-Gln-Leu-Ala-Val-Lys-Lys-Tyr-
Leu-Asn-Ser-Ile-Leu-Asn-NH₂ or a pharmaceutically acceptable salt thereof.

6. The method according to claim 1 wherein R1 is Aib, R2 is Phe, and R3 is Met and said peptide is:

```
                                                  (SEQ ID NO: 5)
His-Ser-Asp-Aib-Val-Phe-Thr-Asp-Asn-Tyr-Thr-Arg-
Leu-Arg-Lys-Gln-Met-Ala-Val-Lys-Lys-Tyr-Leu-Asn-
Ser-Ile-Leu-Asn-NH₂
``` or a pharmaceutically acceptable salt thereof.

7. The method according to claim 1 wherein R1 is Aib, R2 is Phe, and R3 is Leu and said peptide is:

```
His-Ser-Asp-Aib-Val-Phe-Thr-Asp-Asn-Tyr-Thr-Arg-Leu-Arg-Lys-    SEQ ID NO: 6)
Gln-Leu-Ala-Val-Lys-Lys-Tyr-Leu-Asn-Ser-Ile-Leu-Asn-NH₂
``` or a pharmaceutically acceptable salt thereof.

8. The method according to claim 1 wherein R1 is Ac5c, R2 is Phe, and R3 is Leu and said peptide is:

```
His-Ser-Asp-Ac5c-Val-Phe-Thr-Asp-Asn-Tyr-Thr-Arg-Leu-Arg-Lys-    (SEQ ID NO: 7)
Gln-Leu-AlaVal-Lys-Lys-Tyr-Leu-Asn-Ser-Ile-Leu-Asn-NH₂
``` or a pharmaceutically acceptable salt thereof.

9. The method according to claim 1 wherein R1 is Deg, R2 is Phe, and R3 is Leu and said peptide is:

```
His-Ser-Asp-Deg-Val-Phe-Thr-Asp-Asn-Tyr-Thr-Arg-Leu-Arg-Lys-    (SEQ ID NO: 8)
Gln-Leu-Ala-Val-Lys-Lys-Tyr-Leu-Asn-Ser-Ile-Leu-Asn-NH₂
``` or a pharmaceutically acceptable salt thereof.

10. The method according to claim 1 wherein R1 is Aib, R2 is Phe, and R3 is Dpg and said peptide is:

```
His-Ser-Asp-Aib-Val-Phe-Thr-Asp-Asn-Tyr-Thr-Arg-Leu-Arg-Lys-    (SEQ ID NO: 9)
Gln-Dpg-Ala-Val-Lys-Lys-Tyr-Leu-Asn-Ser-Ile-Leu-Asn-NH₂
``` or a pharmaceutically acceptable salt thereof.

11. The method according to claim 1 wherein R1 is Aib, R2 is 4-Cl-D-Phe, and R3 is Dpg and said peptide is:

```
His-Ser-Asp-Aib-Val-4-Cl-D-Phe-Thr-Asp-Asn-Tyr-Thr-Arg-Leu-    (SEQ ID NO: 10)
Arg-Lys-Gln-Dpg-Ala-Val-Lys-Lys-Tyr-Leu-Asn-Ser-Ile-Leu-Asn-NH₂
``` or a pharmaceutically acceptable salt thereof.

12. The method according to claim 1 wherein R1 is Deg, R2 is Phe, and R3 is Dpg and said peptide is:

```
His-Ser-Asp-Deg-Val-Phe-Thr-Asp-Asn-Tyr-Thr-Arg-Leu-Arg-Lys-    (SEQ ID NO: 11)
Gln-Dpg-Ala-Val-Lys-Lys-Tyr-Leu-Asn-Ser-Ile-Leu-Asn-NH₂
``` or a pharmaceutically acceptable salt thereof.

13. The method according to claim 1 wherein R1 is Ac5c, R2 is Phe, and R3 is Dpg and said peptide is:

```
His-Ser-Asp-Ac5c-Val-Phe-Thr-Asp-Asn-Tyr-Thr-Arg-Leu-Arg-Lys-    (SEQ ID NO: 12)
Gln-Dpg-Ala-Val-Lys-Lys-Tyr-Leu-Asn-Ser-Ile-Leu-Asn-NH₂
``` or a pharmaceutically acceptable salt thereof.

14. The method according to claim 1 wherein the cancer is ovarian, colon, lung, oral, pancreatic, or non-small lung, or cancer of the duodenum, or glioblastoma.

\* \* \* \* \*

SEQUENCE LISTING

<160> NUMBER OF SEQ ID NOS: 12

<210> SEQ ID NO 1
<211> LENGTH: 28
<212> TYPE: PRT
<213> ORGANISM: Sus barbatus

```
<400> SEQUENCE: 1

His Ser Asp Ala Val Phe Thr Asp Asn Tyr Thr Arg Leu Arg Lys Gln
  1               5                  10                  15

Met Ala Val Lys Lys Tyr Leu Asn Ser Ile Leu Asn
                20                  25

<210> SEQ ID NO 2
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = alpha-aminoisobutyric acid/label
      = Aib
<220> FEATURE:
<221> NAME/KEY: MOD_RES
<222> LOCATION: (6)
<223> OTHER INFORMATION: /product =4-chloro-D-phenylalanine/label =
      4-Cl-D-Phe

<400> SEQUENCE: 2

His Ser Asp Xaa Val Xaa Thr Asp Asn Tyr Thr Arg Leu Arg Lys Gln
  1               5                  10                  15

Leu Ala Val Lys Lys Tyr Leu Asn Ser Ile Leu Asn
                20                  25

<210> SEQ ID NO 3
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = di-ethyl glycine/label = Deg
<220> FEATURE:
<221> NAME/KEY: MOD_RES
<222> LOCATION: (6)
<223> OTHER INFORMATION: /product = 4-chloro-D-phenylalanine/label =
      4-Cl-D-Phe

<400> SEQUENCE: 3

His Ser Asp Xaa Val Xaa Thr Asp Asn Tyr Thr Arg Leu Arg Lys Gln
  1               5                  10                  15

Leu Ala Val Lys Lys Tyr Leu Asn Ser Ile Leu Asn
                20                  25

<210> SEQ ID NO 4
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = 1-Aminocyclopentane carboxylic
      acid/label = Ac5c
<220> FEATURE:
<221> NAME/KEY: MOD_RES
<222> LOCATION: (6)
<223> OTHER INFORMATION: /product = 4-chloro-D-phenylalanine/label =
      4-Cl-D-Phe
```

<400> SEQUENCE: 4

His Ser Asp Xaa Val Xaa Thr Asp Asn Tyr Thr Arg Leu Arg Lys Gln
 1               5                  10                  15

Leu Ala Val Lys Lys Tyr Leu Asn Ser Ile Leu Asn
            20                  25

<210> SEQ ID NO 5
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = alpha-aminoisobutyric acid/label
      =Aib

<400> SEQUENCE: 5

His Ser Asp Xaa Val Phe Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 6
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = alpha-aminoisobutyric acid/label
      = Aib

<400> SEQUENCE: 6

His Ser Asp Xaa Val Phe Thr Asp Asn Tyr Thr Arg Leu Arg Lys Gln
 1               5                  10                  15

Leu Ala Val Lys Lys Tyr Leu Asn Ser Ile Leu Asn
            20                  25

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = 1-Aminocyclopentane carboxylic
      acid/label = Ac5c

<400> SEQUENCE: 7

His Ser Asp Xaa Val Phe Thr Asp Asn Tyr Thr Arg Leu Arg Lys Gln
 1               5                  10                  15

Leu Ala Val Lys Lys Tyr Leu Arg Ser Ile Leu Asn
            20                  25

<210> SEQ ID NO 8
<211> LENGTH: 28
<212> TYPE: PRT

```
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = di-ethyl glycine/label = Deg

<400> SEQUENCE: 8

His Ser Asp Xaa Val Phe Thr Asp Asn Tyr Thr Arg Leu Arg Lys Gln
 1               5                  10                  15

Leu Ala Val Lys Lys Tyr Leu Asn Ser Ile Leu Asn
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = alpha-aminoisobutyric acid/label
      =Aib
<220> FEATURE:
<221> NAME/KEY: MOD_RES
<222> LOCATION: (17)
<223> OTHER INFORMATION: /product = di-n-propylglycine/label = Dpg

<400> SEQUENCE: 9

His Ser Asp Xaa Val Phe Thr Asp Asn Tyr Thr Arg Leu Arg Lys Gln
 1               5                  10                  15

Xaa Ala Val Lys Lys Tyr Leu Asn Ser Ile Leu Asn
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = alpha-aminoisobutyric acid/label
      =Aib
<220> FEATURE:
<221> NAME/KEY: MOD_RES
<222> LOCATION: (6)
<223> OTHER INFORMATION: /product = 4-chloro-D-phenylalanine/label =
      4-Cl-D-Phe
<220> FEATURE:
<221> NAME/KEY: MOD_RES
<222> LOCATION: (17)
<223> OTHER INFORMATION: /product = di-n-propyglycine/label = Dpg

<400> SEQUENCE: 10

His Ser Asp Xaa Val Xaa Thr Asp Asn Tyr Thr Arg Leu Arg Lys Gln
 1               5                  10                  15

Xaa Ala Val Lys Lys Tyr Leu Asn Ser Ile Leu Asn
            20                  25

<210> SEQ ID NO 11
<211> LENGTH: 28
<212> TYPE: PRT
<213> ORGANISM: Artificial Sequence
```

```
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (4)
<223> OTHER INFORMATION: /product = di-ethylglycine/label = Deg
<220> FEATURE:
<221> NAME/KEY: MOD_RES
<222> LOCATION: (17)
<223> OTHER INFORMATION: /product = di-n-propylglycine/label = Dpg

<400> SEQUENCE: 11

His Ser Asp Xaa Val Phe Thr Asp Asn Tyr Thr Arg Leu Arg Lys Gln
 1               5                  10                  15

Xaa Ala Val Lys Lys Tyr Leu Asn Ser Ile Leu Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated
<220> FEATURE:
<221> NAME/KEY: MOD_RES
<222> LOCATION: (4)
<223> OTHER INFORMATION: /product = 1-Aminocyclopentane carboxylic
      acid/label = Ac5c
<220> FEATURE:
<221> NAME/KEY: MOD_RES
<222> LOCATION: (17)
<223> OTHER INFORMATION: /product = di-n-propylglycine/label = Dpg

<400> SEQUENCE: 12

His Ser Asp Xaa Val Phe Thr Asp Asn Tyr Thr Arg Leu Arg Lys Gln
 1               5                  10                  15

Xaa Ala Val Lys Lys Tyr Leu Asn Ser Ile Leu Asn
            20                  25
```